Figure 1:
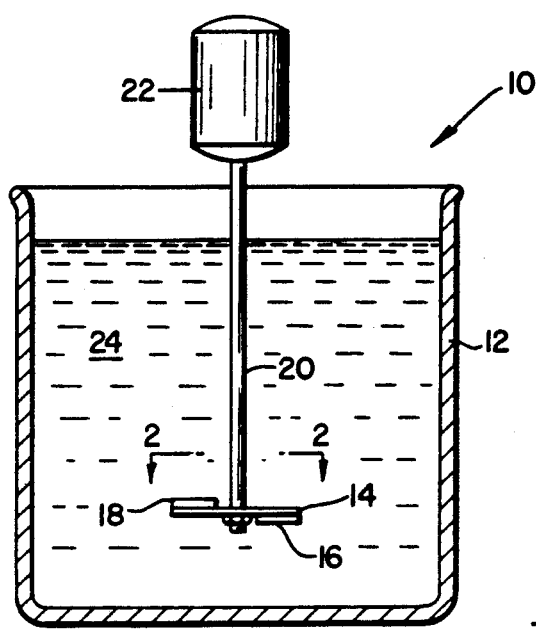

United States Patent [19]

Boulanger et al.

[11] Patent Number: 5,023,247
[45] Date of Patent: Jun. 11, 1991

[54] INSECTICIDAL COATING COMPOSITION AND PROCESSES FOR MAKING AND USING IT

[75] Inventors: Jean-Paul Boulanger; Jacques Lupuyo; Francois Klug, all of Montreal, Canada

[73] Assignee: Insecta Paint, Inc., Burlington, Vt.

[21] Appl. No.: 358,488

[22] Filed: May 30, 1989

Related U.S. Application Data

[63] Continuation of Ser. No. 537,005, Sep. 29, 1983, abandoned, which is a continuation of Ser. No. 409,823, Aug. 20, 1982, abandoned.

[51] Int. Cl.$^5$ .................... A01N 57/00; A01N 31/14; A01N 29/12; A01N 25/26
[52] U.S. Cl. ..................... 514/89; 514/715; 514/748; 424/419
[58] Field of Search .............. 514/86, 89, 748, 975, 514/107, 84, 715; 524/19; 424/81, 354, 419, 78; 106/8; 71/116, 120

[56] References Cited

U.S. PATENT DOCUMENTS

| | | | |
|---|---|---|---|
| 2,632,740 | 3/1953 | Schibler | 524/19 |
| 3,080,280 | 3/1963 | Lidner | 424/354 |
| 3,156,661 | 11/1964 | Feinberg | 424/81 |
| 3,235,366 | 2/1966 | Seymour et al. | 514/748 |
| 3,244,586 | 4/1966 | Rigternik | 514/89 |
| 3,395,028 | 7/1968 | Mackles | 106/8 |
| 3,399,991 | 9/1968 | Littler | 514/975 |
| 4,101,655 | 7/1978 | Sukman | 514/107 |
| 4,303,642 | 12/1981 | Kangas | 424/78 |
| 4,656,163 | 4/1987 | Anderson et al. | 514/86 |
| 4,780,457 | 10/1988 | Tsuboi et al. | 514/89 |

FOREIGN PATENT DOCUMENTS

| | | | |
|---|---|---|---|
| 154508 | 1/1951 | Australia | 424/354 |
| 157920 | 6/1952 | Australia | 424/354 |
| 115805 | 7/1984 | Japan . | |

OTHER PUBLICATIONS

Chemical Abstracts, vol. 110, No. 15, Apr. 10, 1989, (Koho: JP63, 185, 909), Aug. 1, 1988.
Chemical Abstracts, vol. 102, No. 9, Mar. 4, 1985 (Koho: JP 59, 115, 805) Jul. 4, 1984.

*Primary Examiner*—Stanley J. Friedman
*Assistant Examiner*—Kevin E. Weddington
*Attorney, Agent, or Firm*—David R. Murphy; Frank P. Presta

[57] ABSTRACT

A coating composition comprising a first phase containing a cross-linkable resin; a second phase containing water; and a third phase containing an insecticide dissolved in a solvent wherein the solvent is immiscible with the first phase and with water.

These coating compositions kill insects even after exposure to weather for extended periods of time. They have kill rates higher than prior art compositions containing the same amount of the same insecticide.

30 Claims, 1 Drawing Sheet

INSECTICIDAL COATING COMPOSITION AND PROCESSES FOR MAKING AND USING IT

CROSS REFERENCE TO RELATED APPLICATION

This application is a continuation of application Ser. No. 537,005 filed Sept. 29, 1983, now abandoned, which is continuation of application Ser. No. 409,823 filed Aug. 20, 1982, now abandoned.

DISCLOSURE

Insecticidal coating compositions are well known and have been employed for years in order to provide substrates with protective coatings which kill insects upon contact. See for example Feinberg U.S. Pat. No. 3,156,661.

Unfortunately, these prior coating compositions suffer from a number of disadvantages. Perhaps the most serious disadvantage is that while effective immediately after application, they are not effective after standing for a period of time such as 30 days or more. Another disadvantage is that the insecticidal properties of the resultant coating composition is reduced by exposure to rain, to sun, and to the elements. In an attempt to overcome these disadvantages, it has been suggested to increase the amount of the insecticide in the coating composition. However, increasing the amount of insecticide increases the cost of the coating composition and in many cases still does not provide a lasting pathogenic effect.

Accordingly, it is an object of the present invention to provide an improved insecticidal coating composition substantially free of one or more of the disadvantages of prior compositions.

Another object is to provide an improved coating composition which retains its ability to kill insects for long periods of time.

Still another object of the present invention is to provide an improved insecticidal coating composition which retains its ability to kill insects even after exposure to the elements.

Another object is to provide an improved coating composition having long lasting properties for employing only a minor amount of the insecticide.

Still another object is to provide an improved process for providing a substrate with an insecticidal coating.

Yet another object is to provide an improved method for killing insects by contacting them with an insecticidal coating produced by the compositions of the present invention.

Yet another object is to provide an improved process for making insecticidal coating compositions.

The above and other objects are accomplished according to the present invention by providing an insecticidal composition comprising:

A. a first phase containing a cross-linkable resin; and

B. a second phase containing water; and

C. a third phase containing an insecticide dissolved in an insecticide-solvent.

In the coating compositions of the present invention, it is critical that the insecticide-solvent be immiscible with the first phase and, furthermore, it is critical that the insecticide-solvent be immiscible with water.

In one preferred embodiment of the present invention, the third phase is unstable. By this it means that the third phase exhibits the property of separating from the second phase when the coating composition sits under normal conditions for a period of time such as thirty days. By normal conditions it is meant that the coating composition is not agitated and that it sits at atmospheric pressure (760 mg Hg) and room temperature (25° C.; 77° F.). It should be clearly understood that this instability is a property of the coating composition of the present invention and does not describe the form of the composition prior to use. If the third phase has separated then it must be redispersed in the second phase prior to use.

In another preferred embodiment of the present invention, the third phase has a specific gravity less than the mixture of the first and second phase.

The first phase can be free of solvent but most commonly contains a resin-solvent. The resin-solvent is employed to dissolve the resin and is present in an amount sufficieint to dissolve at least some of the resin and to evenly disperse the remaining amount of the resin. Any resin-solvent previously employed to dissolve resins is suitable in the present invention. The preferred resin solvents are organic solvents such as petroleum distillate. Most preferred are petroleum distillates having an atmospheric boiling point of 60° to 90° C.

The cross-linkable resins per se form no part of the present invention. Any known cross-linkable resin employed in prior coating compositions can be employed in the present invention without limitation. Examples of suitable cross-linkable resins include among others raw linseed oil, boiled linseed oil, alkyd resins, urethane resins, polyvinyl latexes, acrylic latexes, polyesters and urea-formaldehyde resins.

Alkyd resins are preferred because of their known water dispersibility. The alkyd resins are well-known class of resins and generally comprise the reaction product of acids such as phthalic acid and polyfunctional alcohols such as ethylene glycol, glycerol, and diethylene glycol. The acid and the alcohol are commonly reacted in the presence of a monoglyceride, a diglyceride, a triglyceride, a fatty acid, a fatty acid alcohol and/or mixtures thereof. In one preferred embodiment, the fatty tail contains conjugated unsaturation known to be dryable in air by reaction with atmospheric oxygen in order to provide a cross-linking reaction. If a urethane resin is used the cross-linkable resin cross-links by reaction with atmospheric moisture.

In a preferred embodiment of the present invention, the first phase is free of surfactants. All surfactants tested to date have imparted undesirable stability to the third phase. The stability of the third phase causes undesirable results. In a preferred embodiment, the third phase is unstable such that it separates when left to stand undisturbed at atmospheric pressure and 25° C. for a period of thirty days. However, it is entirely possible that of the hundreds of thousands of surfactants known today that there may be a few, presently unknown to the inventors, whose presence in the coating composition is not deleterious.

The coating composition comprises the three enumerated phases. Thus the coating compositions can have other ingredients commonly found in coating compositions. These additional ingredients may be present as part of the first phase, the second phase, or the third phase, or may be present as fourth or additional phases. Examples of these additional ingredients include among others pigments, dyes, fillers, stabilizers, antifreezes, thixotropic agents, and/or fungicides. Examples of known pigments include titanium dioxide and calcium carbonate. Examples of fungicides include Dowicil 75 whose chemical name is 1-(-3-chlorollyl)-3,5,7-triaza-1-azoniaadamantane chloride; and Vancide TH, whose chemical name is Hexahydro-1,3,5-triethyl-5-triazine; and Tektamer 38 whose chemical name is 1,2 dibromo-2-4-dicyanobutane.

The second phase contains water and preferably consists essentially of water together with equilibrium amounts of the other ingredients present in the coating composition which are soluble in water. The weight ratio of the first phase to the second phase can vary widely from about 1:10 to 10:1 but is preferably from 1:5 to 5:1. Coating compositions commonly have a certain percent solids measured according to ASTM Test No. D1644-75. The coating compositions of the present invention generally have from 50 to 98 and preferably have from 70 to 90 percent solids.

In the broadest aspects of the present invention, any known insecticide can be employed which is pathogenic to the target organism. Thus, the present invention is effective with insecticides such as dischlorodiphenyl-trichloro-ethane, known as DDT, 1,2,3,4,5,6-hexachlorocyclohexane, known as Lindane, and other chlorinated organic compounds. However, the preferred insecticide is chlorpyrifos whose chemical name is 0,0-diethyl-0-3,5,6-trichloro-2-pyridyl ester. Chlorpyrifos is produced as described in U.S. Pat. No. 3,244,586 and is available from the Dow Chemical Company, Midland, Mich., U.S.A., under the trade name Dursban. Chlorpyrifos is preferred because it is soluble in xylene, a preferred solvent having desirable characteristics. Furthermore, chlorpyrifos is approved by the United States Environmental Protection Agency; and is known to have the desirable pathogenic effect on house flies, American cockroaches, German cockroaches, and ants. Furthermore, chlorpyrifos is known to be an arachnicide. As used herein, the term insecticide is meant to include arachnicides. The present invention provides for a more effective coating composition irrespective of the insecticidal properties of the insecticide employed.

The insecticide-solvent is chosen such than it is immiscible with the first phase and is immiscible with water. Examples of suitable insecticide-solvents include among others methylchloride, ethyl ether, methyl ether and xylene. The others are not preferred because of their flammability and their toxicity; however, they are technologically suitable for use in the present invention. Xylene is the preferred solvent for the insecticide. Xylene is the preferred insecticide-solvent when petroleum distillates are chosen as the resin-solvent. The preferred insecticide-solvents have a specific gravity less than the resin-solvent. The insecticide is present in the coating composition generally in an amount from 0.001 to 4 and preferably from 0.45 to 1.30 percent by weight based on the weight of the coating composition. When much less insecticide is present, the coating compositions are not sufficiently pathogenic. Greater amounts of insecticide are not harmful to the coating composition but render the coating compositions unnecessarily expensive.

The coating compositions of the present invention can be applied to the substrate by any known method such as brushing, rolling, or spraying. Any substrate can be employed such as substrates of wood, metal, masonry, glass, or plastic. Preferably, the applying is conducted at atmospheric pressure and at a temperature of 5° to 40° C. After applying the coating composition, the cross-linkable resin is cross-linked. The cross-linking reaction is characteristic of the resin. When the resin contains conjugated unsaturation, then the cross-linking is effected by the creation of peroxide linkages by reaction with atmospheric oxygen. When the cross-linkable resin is a urethane, the cross-linking reaction occurs by reaction with atmospheric moisture. Each cross-linkable resin has its characteristic cross-linking reaction. After the coating composition has been applied to the substrate and after the cross-linkable resin has been cross-linked, insects are killed simply by contacting them with the cross-linked coating.

The coating compositions of the present invention are produced by a process comprising the steps of: providing a resin-solution and then dispersing the resin-solution in water to from a two-phase dispersion and then adding the insecticide-solution to the two-phase dispersion. If the insecticide is included in either the resin-solution or the water phase, then the results of the present invention are not achieved. The dispersing of the resin-solution in water and the adding of the insecticide solution is preferably accomplished at atmospheric pressure purely for convenience. Any convenient temperature can be employed such as temperatures from 5° C. to 40° C.; however, room temperature of 20° C. is commonly employed for convenience. However, temperatures above 30° C. should not be obtained during the adding of the insecticide-solution or after the insecticide-solution has been added. Temperatures above 30° C. tend to cause undesirable decomposition of certain insecticides.

Figure 2:
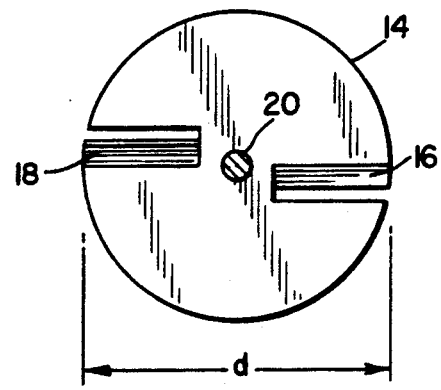
Figure 3:
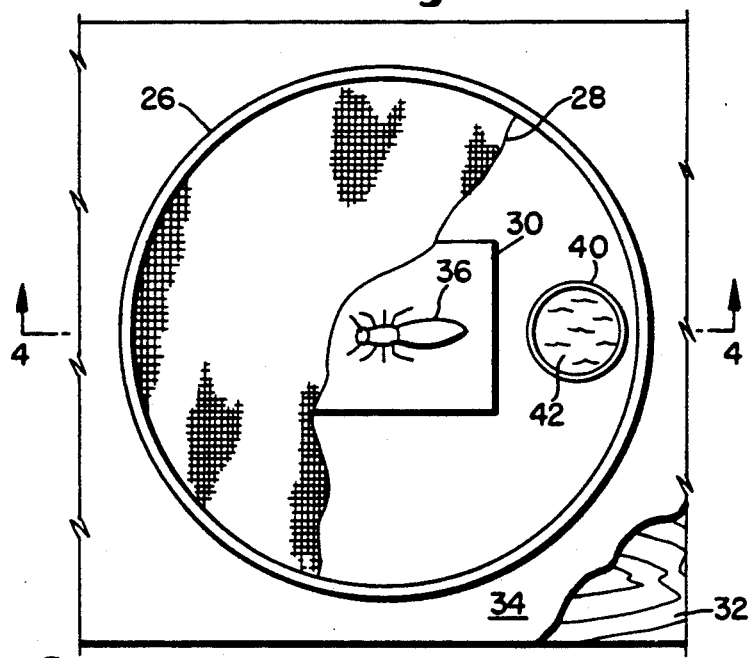
Figure 4:
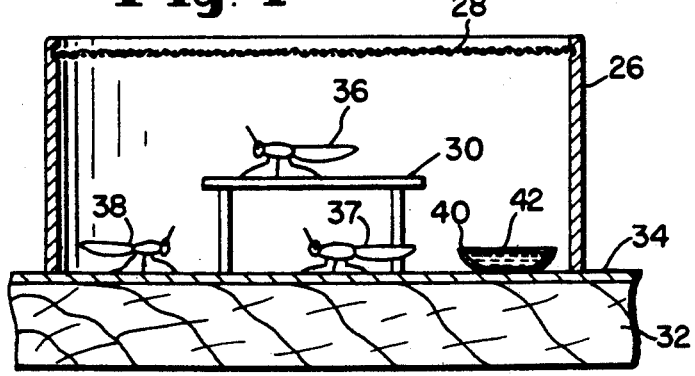
Figure 5:
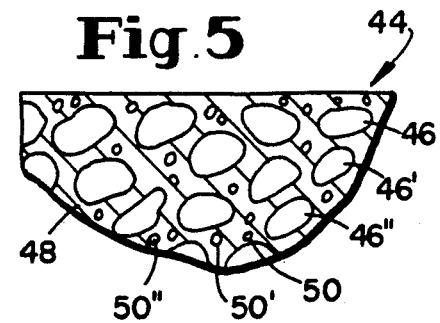

The invention may be better understood by reference to the drawings wherein:

FIG. 1 is a schematic sectional view of a mixing tank equipped with an impeller, which mixing tank is useful for producing the compositions of the present invention; and FIG. 2 is a view of the impeller taken along Line 2—2 of FIG. 1; and FIG. 3 is a top view of a choice box showing the manner in which the compositions of the present invention are tested; and FIG. 4 is a sectional view taken along Line 4—4 of FIG. 3; and FIG. 5 is a schematic representation of the coating composition of the present invention.

Referring now to the drawings in general and to FIGS. 1 and 2 in particular, there is shown an apparatus 10 useful for producing the compositions of the present invention. The apparatus 10 comprises a mixing tank 12. Within the mixing tank 12 is an impeller 14 having two blades 16, 18. The impeller 14 is fixedly attached to a shaft 20 which in turn is attached to a motor 22. When the motor 22 is caused to rotate, the impeller 14 spins with the result that the blades 16, 18 cause mixing of the liquid 24 in the tank 12.

Referring now to FIGS. 3 and 4, there is shown a choice box 26 having an air-permeable screen 28 at its top and having therein and elevated platform 30. In order to test the effectiveness of the insecticidal coating compositions, the composition is painted onto a substrate 32 in order to form a continuous layer 34. The layer 34 is permitted to dry, to cure, and to age for a certain number of days whereupon insects such as the cockroaches 36, 37, 38 are confined into an area on the layer 34. The choice box 36 is so named because any given insect has a choice of remaining on the layer 34 as in the case of the cockroaches 37, 38 or of avoiding contact with the layer 34 by climbing on top of the platform 30 as in the case of the cockroach 36. Underneath the choice box 26 is a watch glass 40 containing a 5 weight percent glucose solution. This solution provides both food and water for the cockroaches 36, 37, 38. The solution is replenished from time to time during any test.

Referring now to FIG. 5, there is shown a schematic representation of the coating composition 44 of the present invention in its condition just prior to use. The coating composition 44 comprises a first phase 46, 46', 46" which contains a cross-linkable resin. The first phase 46, 46', 46" is a discontinuous phase which is dispersed throughout the second phase 48. The second phase 48 is the water-containing phase. The coating composition 44 also contains a third phase 50, 50', 50" which contains the insecticide dissolved in the insecticide solvent. As explained elsewhere herein, the third phase 50, 50', 50" separates on standing but is redispersed as shown in FIG. 5 prior to applying the coating composition 44 to any substrate, such as the substrate 32 shown in FIG. 3 and 4.

The invention may be understood by reference to the following examples wherein all parts and percentages are by weight unless otherwise indicated. These examples are designed to teach those skilled in the art how to practice the invention and to explain the best mode presently known for practicing the invention.

EXAMPLE 1

This example illustrates the synthesis of an insecticide-solution useful in the present invention.

The following quantities of the following ingredients are combined as indicated.

| Item | Name | Parts by Weight |
|------|------|-----------------|
| A | chlorpyrifos | 70 |
| B | xylene | 86 (100 ml) |
| | Total | 156 |

Items A and B are mixed at 20° C. (68° F.) and atmospheric pressure until all of Item A dissolves in Item B to form a mixture referred to herein as "Insecticide Solution A".

Item A employed in this example is the product known as Dursban available from the Dow Chemical Company, Midland, Mich. Dursban comprises 99% by weight 0,0-diethyl-0-3,5,6-trichloro-2-pyridyl ester and 1% by weight of related compounds.

Item B is the commerically available product having the same name which is a mixture of the commonly occurring amounts of the three different position isomers.

EXAMPLE 2

This example illustrates the synthesis of insecticide-free coating composition that is useful in the present invention.

The following quantities of the following ingredients are combined as indicated.

| Item | Name | Parts by Weight |
|------|------|-----------------|
| A | dispersant | 11 |
| B | anti-foam | 0.5 |
| C | ethylene glycol | 63 |
| D | TiO$_2$ | 200 |
| E | CaCO$_3$ | 100 |
| F | ethylene glycol | 30 |
| G | preservative | 0.5 |
| H | acrylic resin dispersion | 200 |
| I | talc | 100 |
| J | water | 123 |
| K | methoxy cellulose | 2 |
| L | diethylene glycol butyl ether acetate | 10 |
| M | triethanolamine | 3 |
| N | magnesium aluminum silicate | 3 |
| O | water | 100 |
| | Total | 946 |

Items A, B, C, D, and E are placed in the mixing tank 12 shown in FIG. 1. The impeller 14 is caused to rotate at 3,000 revolutions per minute for twenty minutes whereupon the speed is reduced to 1,000 revolutions per minute and Items F, G, H, and I are added. Rotation of the impeller 14 is continued at 1,000 revolutions per minute for fifteen minutes whereupon Items J, K, L, and M are added and mixing is continued at the same speed for ten minutes. The speed is then increased to 1,500 revolutions per minute, and Items N and O are added. The speed of the impeller 14 is reduced to 1,000 rpm and mixing continued for an additional fifteen minutes.

The dispersant is that sold under the trade name Tamol 731. The anti-foam is that sold by the Down Corning Coporation under the designation DB-110A. The ethylene glycol functions in the composition as an anti-freeze and affects the viscosity of the composition. The titanium dioxide is a pigment. The calcium carbonate is a filler. The preservative is that sold under the trade name Tektamer 38 and functions as a fungicide.

The acrylic resin dispersion is that sold by the Rhom and Haas Corporation as Rhoplex AC/64 and is a resin dispersed in water with the addition of a solvent. The resin are mixed acrylic acid esters which are cross-linkable upon exposure to air. The dispersion contains 46.4% by weight resin and contains 3.6% by weight of organic solvent. The dispersion (Item H) contains 61% solids. The talc functions as a filler. The methoxy cellulose is a thickener and increases the viscosity. Item L functions as a coalescing agent whereas Item M functions as a surfactant. Item N is a thixotropic agent.

The coating composition produced as described above is termed "Paint X". Paint X is not a coating composition of the present invention because it contains no insecticide. However, it can be employed to produce a coating composition of the present invention as described more completely below.

EXAMPLE 3

This example illustrates the synthesis of a coating composition of the present invention.

Insecticide solution A produced as described in Example 1 herein is added to Paint X produced as described in Example 2 herein until the chlorpyrifos comprises 0.86% by weight of the coating composition. The resultant mixture is a coating composition of the present invention and is termed "Paint A".

EXAMPLE 4

This example is not illustrative of the present invention but illustrates the undesirable results that can occur when a surfactant is added to the insecticide solution.

Five milliliters of alkyl phenoxy poly [ethylene oxy] ethanol produced by the GAF Corporation under the trade name Antarox CTA-639 is added to one hundred milliliters of insecticide solution A in order to produce a composition termed insecticide solution B.

The procedure of Example 3 is then repeated except that insecticide solution A is replaced with insecticide solution B and the resultant paint termed "Paint B". The alkyl phenoxy poly [ethylene oxy] ethanol functions in the composition as a surfactant.

EXAMPLE 5

This comparative example which is not illustrative of the present invention discloses the production of Paint C wherein ethanol is employed as a solvent for the insecticide. Since ethanol is water soluble, it is not a solvent useful in the present invention.

The produce of Example 1 is repeated except that the xylol is replaced with an equivalent weight of ethanol to produce Insecticide Solvent C.

The procedure of Example 3 is then repeated except that Insecticide Solvent A is replaced with an equivalent amount of Insecticide Solvent C to produce Paint C. Paint C is not a coating composition of the present invention, since the insecticide solvent, namely the ethanol, is completely miscible with water.

EXAMPLE 6

This example illustrates the synthesis of Paint D employed as a control, not illustrative of the present invention, which contains xylol alone.

The procedure of Example 3 is repeated except that xylol alone containing no chlorpyrifos and no other insecticide is added in the same amount to Paint X in order to produce Paint D.

EXAMPLE 6

This example illustrates the superior kill rate of compositions of the present invention compared to certain comparative compositions on blattella germanica, commonly known as German cockroaches.

A number of wooden substrates 32 were coated respectively with Paints A, B, C, D, and X. After the coating process, the coated substrates were aged thirty days indoors at room temperature of 20° C. (68° F.) in a well ventilated room, whereupon a choice box 26 containing twenty (20) German cockroaches were trapped underneath in the manner shown in FIG. 3 and 4. The kill rate was determined one day later and the results recorded in Column 4 of Table I; two days later and the results recorded in Column 5 of Table I; and three days later and the results recorded in Column 6 of Table I.

TABLE I

| | | | No. dead after... | | |
|---|---|---|---|---|---|
| 1. Paint | 2. Additive | 3. I or C | 4. 1 day | 5. 2 days | 6. 3 days |
| A | xylol + CP | I | 20 | 20 | 20/11 |
| B | xylol + CP + S | C | 4 | 5 | 5 |
| C | EtOH + CP | C | 6 | 8 | 8 |
| D | xylol | C | 1 | 1 | 1 |
| X | none | C | 2 | 2 | 2 |

KILL RATE ON GERMAN COCKROACHES

Notes
CP means chlorpyrifos
S means surfactant
EtOH means ethanol
I means inventive
C means comparative.

EXAMPLE 7

This example illustrates the unexpectedly high kill rate on periplaneta americana, commonly known as American cockroaches, when they are exposed to coating compositions of the present invention.

A series of wooden panels in the form of substrates 32 were painted with Paints A, B, C, D, and X. The panels were then exposed to the elements by placing them in an area completely exposed to the weather. All panels faced due south and were tilted at an angle of 30 degrees from the horizontal. The test took place in the month of June, 1982, at 45 degress north latitude. The panels were exposed to the weather for thirty days during which time it rained four times, was sunny twenty days and was partly overcast six days.

After the exposure to weather as described above, the panels in the form of substrates 32 were contacted with choice boxes 26 each containing twenty American cockroaches. The kill rate after one day was measured and recorded in Column 4 of Table II; after two days and was recorded in Column 5 of Table II; and after three days and was recorded in Column 6 to Table II.

TABLE II

KILL RATE ON AMERICAN COCKROACHES

| | | | No. dead after... | | |
|---|---|---|---|---|---|
| 1. Paint | 2. Additive | 3. I or C | 4. 1 day | 5. 2 days | 6. 3 days |
| A | xylol + CP | I | 18 | 20 | 20 |
| B | xylol + CP + S | C | 2 | 2 | 3 |
| C | EtOH + CP | C | 2 | 3 | 3 |
| D | xylol | C | 2 | 2 | 4 |
| X | none | C | 2 | 2 | 3 |

Notes
CP means chlorpyrifos
S means surfactant
EtOH means ethanol
I means inventive
C means comparative.

EXAMPLE 8

This example illustrates the unexpectedly high kill rate on musca domestica, commonly known as houseflies.

The procedure of Example 6 was repeated, except that the American cockroaches were replaced with an equal number of houseflies. The results are recorded in Table III.

TABLE III

KILL RATE ON HOUSEFLIES

| | | | No. dead after... | | |
|---|---|---|---|---|---|
| 1. Paint | 2. Additive | 3. I or C | 4. 1 hr. | 5. 2 hrs. | 6. 3 hrs. | 7. 6 hrs. |
| A | xylol + CP | I | 7 | 8 | 13 | 20 |
| B | xylol + CP + S | C | 0 | 2 | 3 | 4 |
| C | EtOH + CP | C | 2 | 2 | 3 | 4 |
| D | xylol | C | 1 | 1 | 1 | 1 |
| X | none | C | 1 | 1 | 3 | 3 |

Notes
CP means chlorpyrifos
S means surfactant
EtOH means ethanol
I means inventive
C means comparative.

EXAMPLE 9

The example illustrates the instability of the third phase of the coating compositions of the present invention.

A container having a volume of 3.84 liters (one U.S. gallon) was filled to within 2 cm of the top with Paint A and then tightly covered. After thirty days, the container was opened and was observed to have Insecticide solution A floating on top. This indicates that while Insecticide Solution A is mechanically dispersed into the mixture, it does not become dissolved in either the continuous phase or the discontinuous phase; nor does Insecticide Solution A form a stable oil-in-water emulsion; nor is Insecticide Solution A miscible with the resin-containing phase.

What is claimed is:

1. A coating composition comprising:
  A. a first liquid phase containing a cross-linkable resin; and
  B. a second liquid phase containing water; and
  C. a third liquid phase containing an insecticide dissolved in an insecticide-solvent;
  with the proviso that:
    (1) the insecticide-solvent is immiscible with the first phase; and
    (2) the insecticide-solvent is immiscible with water; and
    (3) wherein the third phase is free of surfactants.

2. A coating composition comprising:
  A. a first liquid phase containing a cross-linkable resin; and
  B. a second liquid water-containing phase having the first phase dispersed therein; and
  C. a third liquid phase containing an insecticide dissolved in an insecticide-solvent;
  with the provisos that:
    (1) the insecticide-solvent is immiscible with the first phase; and
    (2) the insecticide-solvent in immiscible with water; and
    (3) the third phase is dispersed in the other phases but is unstable such that it exhibits the property of separating from the other phases when the coating composition is permitted to sit unagitated for thirty days at atmospheric pressure and at 25° C; and
    (4) wherein the third phase is free of surfactants.

3. The coating composition of claim 1 wherein the cross-linkable resin is dryable in air.

4. The coating composition of claim 1 wherein the cross-linkable resin cross-links by reaction with atmospheric moisture.

5. The coating composition of claim 1 wherein the cross-linkable resin in an alkyd resin.

6. The coating composition of claim 1 wherein the cross-linkable resin is derived from acrylic acid esters.

7. The coating composition of claim 1 wherein the resin-solvent is an organic solvent.

8. The coating composition of claim 1 wherein the resin-solvent is a petroleum distillate having a boiling point at atmospheric pressure of from 60° to 90° C.

9. The coating composition of claim 1 further comprising pigments, dyes, fillers, stabilizers, anti-freezes, thixotropic agents, and/or fungicides.

10. The coating composition of claim 1 wherein the weight ratio of A:B is 1:10 to 10:1.

11. The coating composition of claim 1 wherein the various components comprise from 50 to 98 percent solids.

12. The coating composition of claim 1 wherein the insecticide is also an arachnicide.

13. The coating composition of claim 1 wherein the insecticide is a chlorinated organic compound pathogenic to the target organism.

14. The coating composition of claim 1 wherein the insecticide is chlorpyrifos.

15. The coating composition of claim 1 wherein the insecticide is 1,2,3,4,5,6 hexachlorocyclohexane.

16. The coating composition of claim 1 wherein the insecticide is dichloro-diphenyl-trichloro-ethane.

17. The coating composition of claim 1 wherein the third phase has a specific gravity less than the mixture of the first and second phases.

18. The coating composition of claim 1 wherein the insecticide-solvent is xylene.

19. The coating composition of claim 1 wherein the weight ratio of the insecticide to the insecticide-solvent is 0.2:1 to 1.5:1 in the third phase.

20. The coating composition of claim 1 wherein the insecticide is present in an amount from 0.001 to 4 percent by weight based upon the weight of the coating composition.

21. An insecticidal coating composition that kills flies and other insects even after exposure to the weather for a period of 30 days, said coating composition comprising:
  A. a first air-dryable cross-linkable resin liquid phase containing a resin which is a member selected from the group consisting of raw linseed oil, boiled linseed oil, alkyd resins, urethane resins, polyvinyl latexes, acrylic latexes, polyesters and urea-formaldehyde resins, said resin being dissolved in an organic solvent; and
  B. a second liquid water phase wherein the first phase is finely dispersed in the second phase; and
  C. a third liquid phase containing chlorpyrifos dissolves in xylene wherein the third phase is free of surfactants; and
  wherein the weight ratio of A:B is 1:5 to 5:1; and
  wherein the third liquid phase separates from the first liquid and second liquid phases when the coating composition is permitted to sit undisturbed at atmospheric pressure and at 25° C. for a period of thirty days; and
  wherein chlorpyrifos comprises from 0.45 to 1.30 percent by weight based on the weight of the coating composition; and
  wherein the third liquid phase has a specific gravity less than that of the mixture of the first liquid and second liquid phases; and
  wherein the weight ratio of the chlorpyrifos to xylene is 0.4:1 to 1.2:1.

22. A process for providing a substrate with an insecticidal coating comprising the steps of:
  I. apply to the substrate a composition comprising:
    A. A first liquid phase containing a cross-linkable resin; and
    B. a second liquid phase containing water; and
    C. a third liquid phase containing an insecticide dissolved in an insecticide-solvent; with the provisos that:
      (1) the insecticide-solvent is immiscible with the first liquid phase; and
      (2) the insecticide-solvent is immiscible with water; and
      (3) the third liquid phase is free of surfactants; and then
  II. Cross-linking the cross-linkable resin.

23. The process of claim 22 wherein the applying is conducted at atmospheric pressure and at a temperature of 5° to 40° C.

24. A process for killing insects comprising the steps of:
   I. applying to the substrate a composition comprising:
      A. a first liquid phase containing a cross-linkable resin; and
      B. a second liquid phase containing water; and
      C. a third liquid phase containing an insecticide dissolved in an insecticide-solvent; with the provisos that:
         (1) the insecticide-solvent is immiscible with the first liquid phase; and
         (2) the insecticide-solvent is immiscible with water; and
         (3) the third liquid phase is free of surfactants; and then
   II. cross-linking the cross-linkable resin to form a cross-linked coating; and then
   III. contacting insects with the cross-linked coating thereby killing them.

25. A process for making a three-phase insecticidal coating composition comprising the steps of:
   I. providing a dispersion of a cross-linkable resin as a first liquid phase dispersed in water as a second liquid phase; and then
   II. adding to the dispersion an insecticide-solution which is the insecticide dissolved in an insecticide-solvent thereby forming a three liquid phase coating composition; with the provisos that:
      (1) the insecticide-solvent is immiscible with the first liquid phase; and
      (2) the insecticide-solvent is immiscible with water; and
      (3) the third liquid phase is free of surfactants.

26. The process of claim 25 wherein Stepp II is practiced at atmospheric pressure and at 5° C. to 40° C.

27. The process of claim 25 wherein Step II is conducted while maintaining the temperature of the coating composition at less than 30° C.

28. A coating composition comprising:
   A. a liquid resin phase, said resin phase comprising a member selected from the group consisting of: raw linseed oil, boiled linseed oil, alkyd resins, urethane resins, polyvinyl latexes, acrylic latexes, polyesters and urea-formaldehyde resins; and
   B. a liquid water phase comprising water; and
   C. a liquid insecticide phase comprising chlorpyrifos and xylene
   wherein the insecticide phase is free of surfactants.

29. A coating composition consisting essentially of:
   A. a first liquid phase of an alkyde resin; and
   B. a second liquid phase of water; and
   C. a third liquid phase of chlorpyrifos dissolved in xylene wherein the insecticide phase if free of surfactants.

30. A three-phase insecticidal coating composition comprising:
   A. an air-dryable, cross linkable liquid resin phase wherein the resin is a member selected from the group consisting of raw linseed oil, boiled linseed oil, alkyd resins, urethane resins, polyvinyl latexes, acrylic latexes, polyesters and urea-formaldehyde resins; and
   B. a liquid water phase; and
   C. an insecticide liquid phase wherein chlorpyrifos is dissolved in an insecticide solvent, said insecticide solvent being a member selected from a group consisting of methylchloride, ethyl ether, methyl ether and xylene;
   wherein the resin phase is dispersed in the water phase forming a dispersion; and
   wherein the insecticide phase has a specific gravity less than that of the dispersion; and
   wherein the weight ratio of A:B is 1:10 to 10:1; and
   wherein the weight ratio of the chlorpyrifos to the insecticide solvent is 0.2:1 to 1.5:1; and
   wherein said insecticide solvent is immiscible with said resin phase; and
   wherein said insecticide solvent is immiscible with water; and
   wherein the third phase is free of surfactants.

* * * * *